United States Patent [19]

Susumu et al.

[11] Patent Number: 4,701,522
[45] Date of Patent: Oct. 20, 1987

[54] NOVEL PROTEIN AND PLANT-VIRUS DISEASE PREVENTIVE AGENTS

[75] Inventors: Kubo Susumu; Ikeda Tsutomu; Takanami Yoichi; Mikami Yoichi, all of Yokohama, Japan

[73] Assignee: Japan Tobacco Inc., Japan

[21] Appl. No.: 815,444

[22] Filed: Dec. 31, 1985

[51] Int. Cl.$^4$ .................... C07K 15/10; A61K 35/78
[52] U.S. Cl. .................................... 530/370; 530/350
[58] Field of Search .................. 530/370, 350; 424/88; 514/2

[56] References Cited

PUBLICATIONS

Ulubelen et al, "Proteinaceous Antitumor Substance from Plants II", J. Pharmaceutical Sci., vol. 55(12), 1966, pp. 1368–1370.

Primary Examiner—John Kight
Assistant Examiner—Garnette D. Draper
Attorney, Agent, or Firm—McGlew and Tuttle

[57] ABSTRACT

It is the object of the invention to provide a chemical substance which is effective, in particular, against insect-transmitted viruses, compared with conventional plant-virus disease preventive agents. This substance is produced from tissues of plants of the genus *Mirabilis*, and may be widely utilized as a basic protein with anti-plant-virus effects and as an active ingredient for plant-virus diseases preventive agents. Such preventive agents can eliminate difficulties in safety, and is effective because antiviral activity is developed systemically.

12 Claims, 1 Drawing Figure

NOVEL PROTEIN AND PLANT-VIRUS DISEASE PREVENTIVE AGENTS

FIELD OF THE INVENTION

This invention relates to a novel basic protein with anti-plant-virus activity, which is obtained from tissues of plants belonging to the genus Mirabilis. It also relates to plant-virus disease preventive agents which contain the above-mentioned protein as an active ingredient.

DESCRIPTION OF THE PRIOR ART

Crops such as tobacco, tomato, green pepper, cucumber, watermelon, radish, Chinese cabbage, etc. cultivated in plowed fields, paddy fields and other facilities are liable to suffer from diseases, including mosaic, dwarf and necrosis, which are caused by tobacco mosaic virus (hereinafter abbreviated as TMV), cucumber mosaic virus (hereinafter abbreviated as CMV), cucumber green mottle mosaic virus (hereinafter abbreviated as CGMMV), potato virus Y (hereinafter abbreviated as PVY) or turnip mosaic virus (hereinafter abbreviated as TuMV), Moreover, these diseases often bring about heavy crop damage. The above viruses originate from infested crops, weeds, trees, seeds, seedlings and soil, and crops are infected through such processes as contact with them during agricultural operations and sap-sucking of insects. As yet, indirect measures have been mainly adopted in order to prevent these virus diseases in crops. Such control measures include eradication or reduction of virus sources, protection of plants from virus-transmitting insects by means of barrier crops or covers, agronomical approaches such as cultivation of resistant varieties, and eradication of vectors by using soil disinfectants and insecticides. The sodium alginate agent (Japanese Pat. No. 717594; Japanese Agriculture, Forestry and Fisheries Ministry Registration No. 13440) and a *Lentinus edodes* mycelium culture extract (Japanese Pat. No. 1012014; Japanese Agriculture, Forestry and Fisheries Ministry Registration No. 15584) have been used as agricultural chemicals against plant viruses. However, both agents are effective only for TMV, which is a contact-transmitted virus, and do not exhibit antiviral activity systemically. Therefore, they have the disadvantage of being ineffective against insect-transmitted viruses which are liable to cause heavy damages in various crops.

SUMMARY OF THE INVENTION

It is an object of the invention to provide a chemical substance which can overcome the disadvantages of conventional plant-virus disease preventive agents as described above and, particularly, which is effective against insect-transmitted viruses.

We carried out screening tests on various materials centering on natural substances in order to develop agents which can eliminate difficulties in safety, and which allow antiviral activity to be realized systemically and also act effectively against insect-transmitted viruses. These tests led us to the findings that a protein contained in the roots, stems, leaves and other tissues of plants belonging to the genus Mirabilis of Nyctaginaceae of Chenopodiales showed an excellently high antiviral activity.

The plants of Mirabilis to be emloyed in the present invention include *Mirabilis jalapa*, *M. longiflora* and *M. nyctaginea*. Infectious diseases of crops including tobacco, tomato, green pepper, cucumber, watermelon, radish, Chinese cabbage, etc. caused by viruses such as TMV, CMV, CGMMV, PVY, TuMV, etc. can be effectively prevented by means of crude sap prepared by grinding tissues of the above-mentioned Mirabilis plants after adding water or a buffer solution (hereinafter simply referred to as buffer). Dilute solutions of crude extracts or refined material which are obtained from the crude sap through the procedure described later can also be utilized. In practice, these liquids are sprayed upon or applied to the stems and leaves or allowed to be absorbed through the roots of the crops. In particular, the protein is highly effective for preventive viral infection caused by sap-sucking insect vectors such as aphids because the antiviral activity of the plants of Mirabilis is developed systemically in the treated plants, unlike the existing saccharide and protein agents. These facts were confirmed experimentally in producing the invention.

The plant-virus disease preventive agents according to the present invention can be widely utilized in the fields of agriculture and horticulture in order to prevent virus diseases.

DETAILED EXPLANATION OF THE INVENTION

Figure 1:
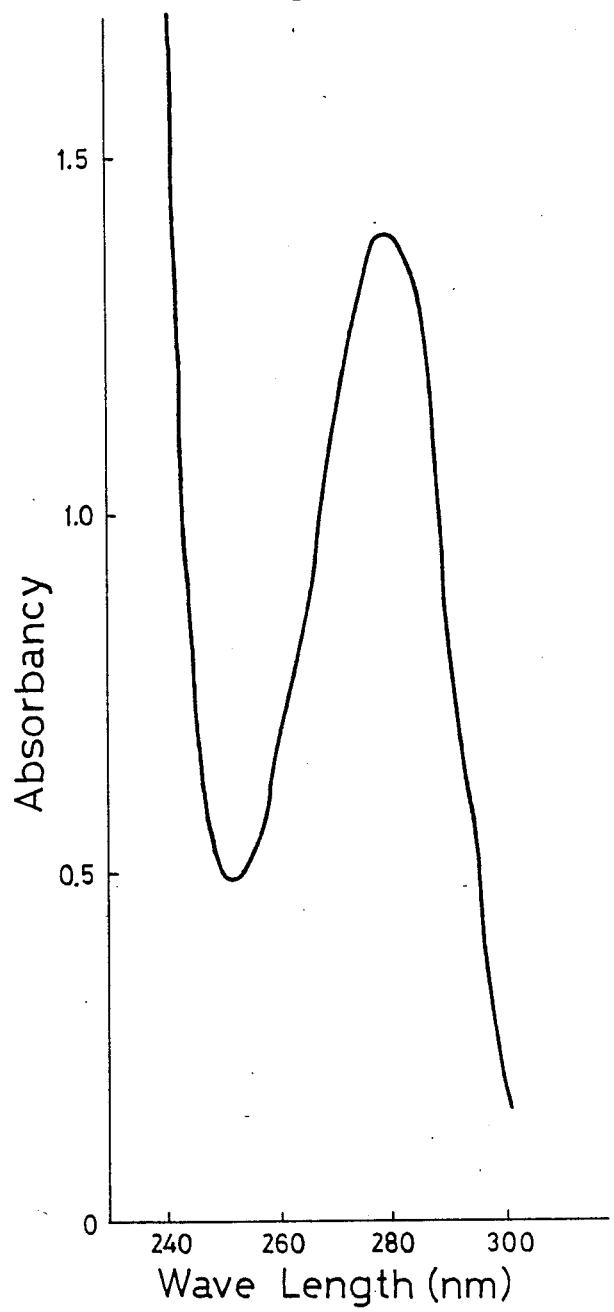
FIG. 1 shows an ultraviolet absorption spectrum of a purified product of the present invention (concentration: 1.55 mg/ml 0.01M phosphate buffer, pH 6.0).

Some examples concerning extraction and purification of the protein of the invention along with its physicochemical properties are described in detail below. Here, roots of Mirabilis plants are mainly used as the material.

One (1) Kg portion (about 5 Kg in terms of fresh weight) of air-dried or freeze-dried roots of Mirabilis plants was milled to provide a powder material. Then it was ground by a mixer or a homogenizer after 20 l volume of 0.01M phosphate buffer (pH 7.2) containing 0.1% of 2-mercaptoethanol was added. The homogenate obtained was centrifuged for 15 minutes at 5,000×g and separated into a supernatant and a sediment. An additional 10 l volume of the above-mentioned extraction solvent was added to the sediment and stirring was carried out adequately. It was then subjected to centrifugal separation for 15 minutes at 5,000×g. Both supernatant portions obtained from the two centrifugal procedures were combined. Ammonium sulfate was poured into it to provide a solution of 50% saturation. Then centrifugal separation was carried out for 15 minutes at 5,000×g, and the supernatant was recovered. Additional ammonium sulfate was added to the supernatant to provide a solution of 90% saturation. Centrifugal separation was performed again under the same conditions as above and a precipitate was obtained. This precipitate was dissolved in a small volume of deionized water, and the material was lyophilized after being dialyzed against deionized water. The crude extract obtained is hereinafter referred to as 90% ammonium sulfate precipitate. Approximately 7.5 g of 90% ammonium sulfate precipitate was obtained per 1 kg of dried roots of Mirabilis plants.

A crude extract having an antiviral activity can also be produced through precipitation by means of acetone or ethanol, as described below. Acetone or ethanol is added to the above-mentioned supernatant of the centrifuged buffer-homogenate prepared from roots of Mirabilis plants in order to provide a 50% and a 75% (volume percent) solution, respectively. The sediment formed is collected through centrifugal separation and then lyophilization processing is carried out to produce a crude extract (hereinafter referred to as 50% acetone precipitate or 75% ethanol precipitate). Thus, 38.4 g of 50% acetone precipitate or 53.8 g of 75% ethanol precipitate was yielded from a 1 kg portion of dried roots of Mirabilis plants. In addition to these procedures using precipitation processes, there is another approach for preparing a crude extract, in which the above-mentioned supernatant of centrifuged crude sap is passed through a cation exchange carrier such as CM-Sepharose mentioned below so that the active ingredient is adsorbed to the carrier. Then elution is conducted under appropriate conditions, and the eluate is concentrated to produce a crude extract.

The precipitates formed above with ammonium sulfate, acetone, ethanol and the like were subjected to column chromatography in order to obtain much purer active ingredient. A crude extract was first dissolved in 0.01M phosphate buffer, pH 6.0, and the solution was passed through a column packed with CM-Sepharose CL-6B (trade name; mfd. by Pharmacia Fine Chemicals) for the active ingredient to be adsorbed. Elution processes were carried out by using NaCl solutions with linear concentration gradients in the range of 0.025 to 0.4M. Active properties were observed in the fractions obtained with NaCl solutions in the range of 0.15 to 0.18M. The active fractions were collected, dialyzed against 0.01M phosphate buffer, pH 7.0, and then passed through a column packed with DEAE-Sepharose (trade name; mfd. by Pharmacia Fine Chemicals) which had been equilibrated with the same buffer as above. The fractions eluted from the column were collected and adjusted to pH 6.0, and the CM-Sepharose column chromatography as described above was carried out again. A single peak having the antiviral activity was obtained through this column chromatographic procedure. Finally, the products were collected, dialyzed against deionized water and lyophilized to provide a purified material. This purified material was yielded at the rate of 87.5 mg per 1 Kg of dried roots of Mirabilis plants. Ultraviolet absorption characteristics of the substance obtained were examined and an absorption spectrum with a peak at the wave length of 280 nm, typical of proteins, was observed as shown in FIG. 1. Its color reactions to the nynhydrin test and the phenol sulfuric acid test proved positive and negative, respectively. An amino acid analysis was carried out for a hydrolysis of this substance, and it was revealed that the substance was a polypeptide having a high content of lysine. Furthermore, the isoelectric point of the substance was investigated by using Carrier Ampholine (trade name; mfd. by LKB-Produkter AB), and values of pI in the range of 9–10 pH were observed. The SDS-polyacrylamide gel electrophoresis was carried out, indicating that the substance had a molecular weight of $2.42 \times 10^4$. This value agreed well with the calculation based on Table 1, which gave a molecular weight of $2.41 \times 10^4$. Finally, the ultracentrifugal analysis was performed, indicating that the sedimentation coefficient, $S_{20W}$, was 2.5. Thus, it was concluded that this substance was a basic protein.

TABLE 1

| Amino Acid | Number of Residual Groups |
| --- | --- |
| lysine | 20 |
| arginine | 6 |
| aspartic acid | 22 |
| threonine | 24 |
| serine | 19 |
| glutamic acid | 19 |
| proline | 8 |
| glycine | 12 |
| alanine | 18 |
| valine | 12 |
| cysteine | 1 |
| methionine | 3 |
| isoleucine | 16 |
| leucine | 18 |
| tyrosine | 10 |
| phenylalanine | 10 |
| tryptophane | 1 |

Note (1) The analysis of tryptophan was carried by absorptiometry.
Note (2) Amides are included in "aspartic acid" and "glutamic acid".

The virus disease prevention procedure by means of the active ingredient obtained from plants of the genus Mirabilis is described below.

A purified material is not necessarily required in the actual application of the active ingredient to crops. Unrefined materials such as a supernatant of centrifuged sap of ground plant tissue, ammonium sulfate precipitate, acetone precipitate, and ethanol precipitate can also be utilized after being diluted. Water-soluble powder, wettable powder and granule can be formed by adding stickers, surfactants, carriers and stabilizers to the above materials according to conventional procedures for producing agricultural chemicals. When they are applied against contact-transmitted viruses such as TMV and CGMMV, it is effective to spray them over the nurseries or the fields in advance of agricultural operations which require direct contact with the crops, including such tasks as transplanting, soilmulching, removing side shoots, tying and harvesting. If the disease preventive agents are to be used against insect-transmitted viruses such as CMV, PVY and TuMV, effective prevention can be carried out by repeating the treatment of crops at intervals of about one week in advance of the migrating season of the insects. The agents according to the present invention cause no damages in the treated plants and had no harmful effects on their growth.

EMBODIMENTS OF THE INVENTION

The effects of this invention are described below by presenting some examples of plant-virus disease prevention tests which were carried out with the active ingredient of Mirabilis plants. However, the descriptions in these examples are not to be considered as limitations, since many changes in the details may be made without departing from the spirit of the invention.

EXAMPLE 1

The antiviral activities of a supernatant of a centrifuged homogenate prepared by grinding the leaves or roots of Mirabilis plants after adding 0.01M phosphate buffer with 0.1% 2-mercaptoethanol (hereinafter referred to as buffer extract) as well as the above-mentioned ammonium sulfate precipitate, acetone precipitate, ethanol precipitate and purified material were tested for TMV, CGMMV, CMV and TuMV. The tests were carried out with plants which are liable to develop local lesions if a virus is inoculated. Specifically, tobacco (Nicotiana tabacum cv. Xanthi-nc) and Jimsonweed (*Datura stramonium*) were used for TMV and CGMMV, respectively, while tobacco (*Nicotiana tabacum* cv. Bright Yellow) was employed for CMV and TuMV. These plants had been cultivated in pots of 12 cm diameter. Each test liquid was applied with a paintbrush to a half area of the upper or under surface of an expanded leaf bounded by the mid-rib while water was applied on the other half as a reference. Each virus was inoculated in a day after the treatment, by applying it over the entire surface of the leaf. The concentrations of inoculated TMV and CMV were 0.05 μg/ml and 5 μg/ml, respectively, while 1/5,000 and 1/100 dilute solutions of sap of diseased leaves were employed for CGMMV and TuMV, respectively. The number of local lesions which appeared on each inoculated leaf in 3–7 days after the virus inoculation were counted and the degree of inhibition was calculated by the following equation.

plants have extremely high degree of inhibition in any combination of virus and plant.

TABLE 2

| Virus | Sample | Concentration | Test Plant | Application Side of Leaf | Degree of inhibition |
|---|---|---|---|---|---|
| TMV | buffer extract prepared from fresh leaves | 1/50 | tobacco (*Nicotiana tabacum* cv. Xanthi-nc) | under surface | 56 |
|  | buffer extract prepared from fresh roots | " | tobacco (*Nicotiana tabacum* cv. Xanthi-nc) | under surface | 64 |
|  | 90% ammonium sulfate precipitate | 1.0 mg/ml | tobacco (*Nicotiana tabacum* cv. Xanthi-nc) | under surface | 94 |
|  | 50% acetone precipitate | " | tobacco (*Nicotiana tabacum* cv. Xanthi-nc) | under surface | 85 |
|  | 75% acetone precipitate | " | tobacco (*Nicotiana tabacum* cv. Xanthi-nc) | under surface | 91 |
|  | purified material | 0.004 mg/ml | tobacco (*Nicotiana tabacum* cv. Xanthi-nc) | under surface | 31 |
|  | " | 0.02 mg/ml | tobacco (*Nicotiana tabacum* cv. Xanthi-nc) | under surface | 63 |
|  | " | 0.1 mg/ml | tobacco (*Nicotiana tabacum* cv. Xanthi-nc) | under surface | 95 |
|  | " | 0.0008 mg/ml | tobacco (*Nicotiana tabacum* cv. Xanthi-nc) | upper surface | 98 |
|  | " | 0.04 mg/ml | tobacco (*Nicotiana tabacum* cv. Xanthi-nc) | upper surface | 100 |
| CGMMV | buffer extract prepared from dried roots | 1/50 | Jimsonweed (*Datura stramonium*) | under surface | 59 |
|  | buffer extract prepared from dried roots | 1/500 | Jimsonweed (*Datura stramonium*) | upper surface | 98 |
|  | buffer extract prepared from dried roots | 1/100 | Jimsonweed (*Datura stramonium*) | " | 100 |
| CMV | 90% ammonium sulfate precipitate | 1.0 mg/ml | tobacco (*Nicotiana tabacum* cv. Bright Yellow) | under surface | 95 |
|  | " | 0.1 mg/ml | tobacco (*Nicotiana tabacum* cv. Bright Yellow) | upper surface | 100 |
| TuMV | 90% ammonium sulfate precipitate | 1.0 mg/ml | tobacco (*Nicotiana tabacum* cv. Bright Yellow) | under surface | 82 |
|  | 90% ammonium sulfate precipitate | 0.1 mg/ml | tobacco (*Nicotiana tabacum* cv. Bright Yellow) | upper surface | 100 |

(Note) The concentrations shown in fraction indicate dilutions taking the weight of the material plant as basis.

$$\text{Degree of inhibition} = \left(1 - \frac{\text{number of local lesions on treated half leaf}}{\text{number of local lesions on control half leaf}}\right) \times 100$$

The results of the test are shown in Table 2. It can be seen that the sample liquids prepared from Mirabilis

EXAMPLE 2

The example described below shows that the effects of the active ingredient contained in Mirabilis plants are exhibited systemically in the treated plants. A solution of 50% acetone precipitate prepared from roots of Mirabilis plant, 1 mg/ml in concentration, was sprayed on five lower leaves of each tobacco plant (*Nicotiana tabacum* cv. Xanthi-nc) in a zone, which were 57 days old after the sowing and approximately 45 cm in height. The three leaves immediately above the treated leaves in each plant were inoculated in one day or three days after the spraying to the latter, by applying a TMV solution of 0.05 μg/ml in concentration. Water was sprayed on the untreated control. The number of local lesions which had developed three days after the inoculation of TMV was counted, and the dregree of inhibition was calculated according to the procedure shown in Example 1. It is obvious from Table 3 that the treatment on some of leaves of a tobacco plant with this active ingredient resulted in a decrease in the number of local lesions on untreated leaves of the same plant. These results lead to the conclusion that the active ingredient of this invention has systemic effects.

TABLE 3

| Zone | Days after Spraying | Number of local lesions/Leaf | Degree of inhibition |
|---|---|---|---|
| Untreated control | — | 521.5 | — |
| 50% acetone precipitate sprayed (this invention) | 1 | 128.8 | 75 |
| 50% acetone precipitate sprayed | 3 | 138.1 | 74 |

TABLE 3-continued

| Zone | Days after Spraying | Number of local lesions/Leaf | Degree of inhibition |
|---|---|---|---|
| (this invention) | | | |

EXAMPLE 3

The inhibitory activity of the present active ingredient against virus transmission by aphid vectors was tested as described below. A solution of 90% ammonium sulfate precipitate or 50% acetone precipitate, 1 mg/ml in concentration, was sprayed on the entire surface of stems and leaves of tobacco plants (*Nicotiana tabacum* cv. Burley 21) and turnip (*Brassica rapa* cv. Kanamachikokabu) cultivated in pots. CMV, PVY or TuMV was inoculated to each plant in a day after the spraying by means of greenpeach aphid (*Myzus persicae*) vectors. Water was sprayed instead on the untreated control. Apterous greenpeach aphids which had been starved for two hours at 25° C. were employed for the inoculation procedure, in which five vectors per plant were released on the test plants after being allowed for ten minutes to probe virus-infected plants (tobacco for CMV and PVY, and turnip for TuMV). The symptoms on the inoculated plants were observed for more than two weeks after the virus inoculation, and the effects of the treatment were determined by comparing the proportion of diseased plants between the treated and untreated. For any of CMV, PVY and TuMV, this active ingredient showed excellent effects against infection through aphid vectors as can be seen from the results in Table 4.

TABLE 4

| Virus | Plot | Test Plant | Proportion of Infected Plants (%) |
|---|---|---|---|
| CMV | Untreated control | tobacco (*Nicotiana tabacum* cv. Burley 21) | 60 |
| | 90% ammonium sulfate precipitate sprayed (this invention) | tobacco (*Nicotiana tabacum* cv. Burley 21) | 20 |
| | Non-inoculated control | tobacco (*Nicotiana tabacum* cv. Burley 21) | 0 |
| PVY | Untreated control | tobacco (*Nicotiana tabacum* cv. Burley 21) | 70 |
| | 50% acetone precipitate sprayed (this invention) | tobacco (*Nicotiana tabacum* cv. Burley 21) | 20 |
| | Non-inoculated control | tobacco (*Nicotiana tabacum* cv. Burley 21) | 0 |
| TuMV | Untreated control | turnip (*Brassica rapa* cv. Kanamachikokabu) | 50 |
| | 90% ammonium sulfate precipitate sprayed (this invention) | turnip (*Brassica rapa* cv. Kanamachikokabu) | 20 |
| | Non-inoculated control | turnip (*Brassica rapa* cv. Kanamachikokabu) | 0 |

What we claim is:

1. A basic protein, which is produced by the process of purifying the extract obtained by extraction of tissue of plants of the genus Mirabilis with a water-soluble solvent, wherein the physicochemical properties comprise:
   a. a peak in the ultraviolet absorption spectrum at a wave length of 280 nm,
   b. a positive ninhydrin reaction and a negative phenol sulfuric acid reaction,
   c. an isoelectric pH of 9 to 10,
   d. a molecular weight of $2.42\times10^4$ as determined by SDS-polyacrylamide gel electrophoresis, and
   e. a sedimentation coefficient of 2.5 as determined by ultracentrifugal analysis, and wherein the amino acid composition comprises:

| Amino Acid | Number of Residual Groups |
|---|---|
| lysine | 20 |
| arginine | 6 |
| aspartic acid | 22 |
| threonine | 24 |
| serine | 19 |
| glutamic acid | 19 |
| proline | 8 |
| glycine | 12 |
| alanine | 18 |
| valine | 12 |
| cysteine | 1 |
| methionine | 3 |
| isoleucine | 16 |
| leucine | 18 |
| tyrosine | 10 |
| phenylalanine | 10 |
| tryptophane | 1. |

2. The protein of claim 1 in the form of an ammonium sulfate precipitate.

3. The protein of claim 1 in the form of an acetone precipitate.

4. The protein of claim 1 in the form of an ethanol precipitate.

5. The protein of claim 1 in the form of a cation exchange carrier purified product.

6. Composition comprising the protein of claim 1 in combination with an aqueous liquid.

7. Composition comprising the protein of claim 1 in combination with a powder or granule material.

8. Composition comprising the protein of claim 1 as active ingredient in an effective amount for inhibiting at least one of toacco mosaic virus (TMV), cucumber mosaic virus (CMV), cucumber green mottle mosaic virus (CGMMV), potato virus Y (PVY), and turnip mosaic virus (TuMV), in combination with an aqueous liquid.

9. Composition comprising the protein of claim 1 as active ingredient in an effective amount for inhibiting at least one of tobacco mosaic virus (TMV), cucumber mosaic virus (CMV), cucumber green mottle mosaic virus (CGMMV), potato virus Y (PVY), and turnip mosaic virus (TuMV), in combination with a powder or granule material.

10. Method of inhibiting at least one of tobacco mosaic virus (TMV), cucumber mosaic virus (CMV), cucumber green mottle mosaic virus (CGMMV), potato virus Y (PVY), and turnip mosaic virus (TuMV) in plants susceptible thereto, which comprises applying to such a plant an effective inhibiting amount of the protein of claim 1.

11. Method of claim 10 wherein the protein is applied in combination with an aqueous liquid.

12. Method of claim 10 wherein the protein is applied in combination with a powder or granule material.

* * * * *